Patented Feb. 28, 1939

Plant Pat. 316

UNITED STATES PATENT OFFICE

316

CHERRY

Lewis Benjamin Reber, Royalton Township, Berrien County, Mich., assignor to The Greening Nursery Company, Monroe, Mich., a corporation No Drawing. Application February 25, 1938, Serial No. 192,671

1 Claim. (Cl. 47—62)

My present discovery relates to cherries of the so-called sour class and particularly to the Montmorency type.

This new variety originated as a limb sport of a Montmorency tree on my home farm and is, in every respect except the ripening date, identical with the parent tree. The ripening date of this new variety, however, is from seven to ten days earlier than that of the Montmorency. The variety has been asexually reproduced through several generations and its early ripening characteristic has persisted.

No drawings are submitted because drawings would disclose nothing, the ripening date being the only claim to novelty.

Following is given a more detailed description of this new variety, the description also applying to the Montmorency cherry. Color plate references are to Ridgway's Color Standards and Nomenclature.

*The plant*

Foliage:

Plentiful.

*Leaves.*—Size—medium, average 3½ inches long and 1½ inches wide. Form—long, oval. Texture—firm, rather heavy, smooth. Color—upper surface, Forest Green (Plate XVII) to Dark Cress Green (Plate XXXI). Under surface, Light Elm Green (Plate XVII). Midrib much lighter green on under side. Veins—prominent. Margin—doubly serrate. Apex—pointed.

*Petiole.*—Strong, ½ to 1 inch long, sometimes tinged with reddish brown.

*The fruit*

Size:

Medium $\frac{11}{16}$ to $\frac{13}{16}$ inch in diameter.

Color:

Scarlet red to Carmine, turning almost Oxblood red before deteriorating (Plate I).

Form:

Oblate spheroid. Broad base. Cavity rather deep. Suture scarcely discernible.

Skin:

Thin but tough. Smooth and glossy.

Flesh:

Very juicy but firm. Translucent.

Flavor:

Slightly acid.

Quality:

Excellent.

Stem:

Medium length, averaging 1¼ inches. Slender.

Seed:

Small, rounded, ⅜ inch long, the same in width, but not quite so thick. Smooth and free from flesh. Cream Buff in color (Plate XXX).

*Comparisons*

The known variety of cherry most nearly like my new variety is the Montmorency which is identical with my variety in every respect except the ripening dates.

Another variety of cherry which is somewhat similar to my variety is the subject of Plant Patent Number 30. The ripening dates of these two varieties are about the same but the growth characteristics of tree and leaf are somewhat different and the fruit itself differs materially, in that my new variety is of the true Montmorency type with translucent flesh and juice, while the subject of Plant Patent Number 30 has fruit of crimson flesh and juice.

A third variety broadly similar to mine is the Richmorency. My variety differs from Richmorency mainly in that the latter is inconsistent in its ripening season—some years ripening its fruit a little in advance of Montmorency and in other years ripening at practically the same date as Montmorency.

Having thus discovered my discovery, I claim:

The new variety of cherry as described, characterized particularly by the early ripening dates of its fruit as compared with the Montmorency cherry.

LEWIS BENJAMIN REBER.